United States Patent

Jensen

Patent Number: 5,827,213
Date of Patent: Oct. 27, 1998

[54] HEEL AND ELBOW DRESSING

[75] Inventor: Ole R. Jensen, 646 Orangeburg Rd., River Vale, N.J. 07675

[73] Assignee: Ole R. Jensen, Northvale, N.J.

[21] Appl. No.: 545,252

[22] Filed: Oct. 19, 1995

[51] Int. Cl.$^6$ .................................................. A61F 13/00
[52] U.S. Cl. ............................... 602/62; 602/54; 602/57; 128/889
[58] Field of Search .................................. 128/881, 889, 128/890, 892; 602/26, 41–45, 54–59, 60–63, 65, 66

[56] References Cited

U.S. PATENT DOCUMENTS

| | | |
|---|---|---|
| 1,845,630 | 2/1932 | School . |
| 2,401,714 | 6/1946 | Weil . |
| 2,443,481 | 6/1948 | Sene . |
| 2,875,758 | 3/1959 | Fuzak et al. . |
| 3,011,494 | 12/1961 | McGowan ............................... 128/892 |
| 3,339,546 | 9/1967 | Chen . |
| 3,357,425 | 12/1967 | Morgan . |
| 3,530,598 | 9/1970 | Kamborian ................................ 36/68 |
| 4,214,582 | 7/1980 | Patel . |
| 4,231,369 | 11/1980 | Sorenson et al. . |
| 4,477,325 | 10/1984 | Osburn ............................... 204/159.12 |
| 4,612,230 | 9/1986 | Liland et al. . |
| 4,650,705 | 3/1987 | Ghadsian ................................ 428/40 |
| 4,674,510 | 6/1987 | Sneider . |
| 4,699,134 | 10/1987 | Samuelsen . |
| 4,702,237 | 10/1987 | Gianopoulos et al. . |
| 4,738,257 | 4/1988 | Meyer et al. . |
| 4,867,146 | 9/1989 | Krupnick et al. . |
| 4,867,748 | 9/1989 | Samuelsen . |
| 5,000,172 | 3/1991 | Ward . |
| 5,008,110 | 4/1991 | Benecke et al. ........................ 424/448 |
| 5,012,801 | 5/1991 | Feret . |
| 5,115,801 | 5/1992 | Cartmell et al. . |
| 5,133,821 | 7/1992 | Jensen . |
| 5,152,282 | 10/1992 | Elphich et al. .......................... 604/180 |
| 5,250,043 | 10/1993 | Castellana et al. . |
| 5,295,950 | 3/1994 | Godley ...................................... 602/53 |
| 5,356,372 | 10/1994 | Donovan et al. . |

FOREIGN PATENT DOCUMENTS

| | | |
|---|---|---|
| 0 621 042 | 10/1994 | European Pat. Off. ........ A61L 15/60 |
| 94 15 058 U | 3/1994 | Germany . |
| A-2 148 125 | 5/1985 | United Kingdom . |
| A-2 191 403 | 12/1987 | United Kingdom . |
| WO 92/05755 | 4/1992 | WIPO ............................. A61F 13/00 |
| WO 93/00056 | 1/1993 | WIPO . |
| WO 93/08777 | 5/1993 | WIPO . |
| WO 95/14451 | 6/1995 | WIPO . |

*Primary Examiner*—Richard J. Apley
*Assistant Examiner*—Kim M. Lee
*Attorney, Agent, or Firm*—McDonnell, Boehnen Hulbert & Berghoff

[57] ABSTRACT

A wound dressing is disclosed that is intended to be supplied to the user in generally planar condition and may then be easily shaped to conform with a joint surface, such as a heel or elbow, without forming wrinkles in that portion of the dressing overlying the wound and without causing potential leakage channels or gaps in the border portion of the dressing surrounding the wound. The dressing includes a layer of pliant adhesive material having particles of one or more water-absorbable and swellable hydrocolloids dispersed therein and a backing layer of a flexible (preferably elastomeric) material extending over one side of the adhesive layer. The dressing is contoured to provide a continuous border in which the adhesive layer has a thickness substantially less than in the central body portion of the dressing. At least one generally triangular gusset portion (preferably two or more of such portions) extends from the border into the central body portion, with the thickness of the adhesive material in the gusset portion(s) being substantially the same as in the border. Each gusset portion may be folded upon itself in use to form a permanent non-expanding triangular pleat for pre-forming the planar dressing into non-planar anatomically-conforming shape.

27 Claims, 1 Drawing Sheet

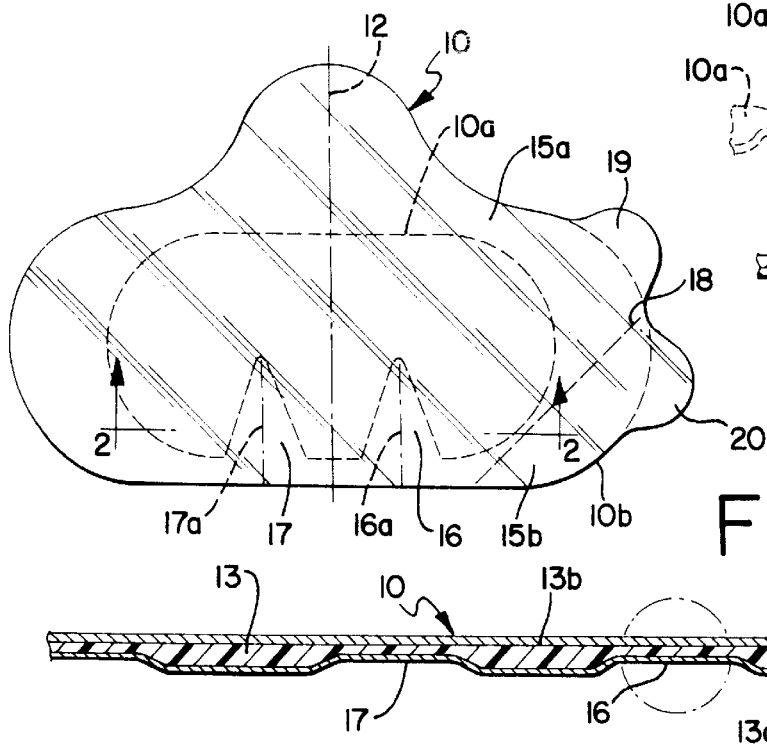
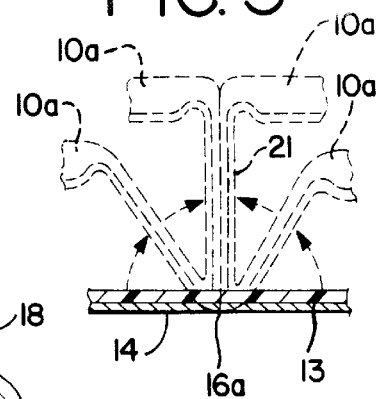
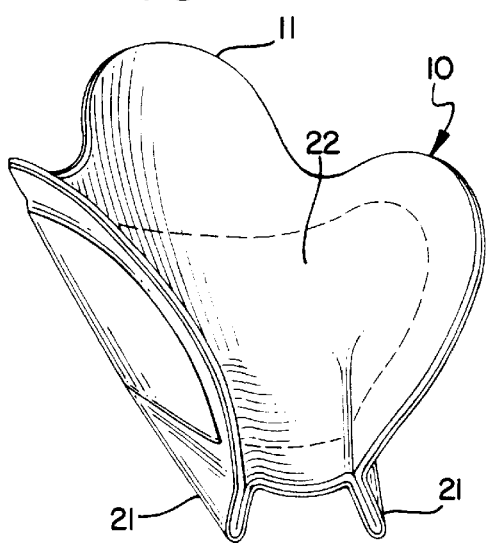
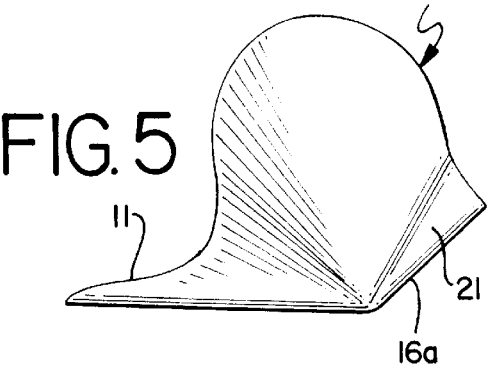
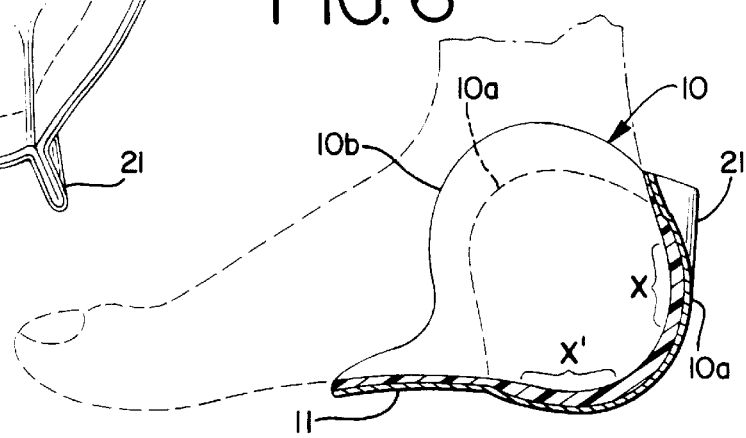

HEEL AND ELBOW DRESSING

BACKGROUND AND SUMMARY

Patients confined to bed or wheelchair frequently experience painful pressure sores and dermal ulcers. Dressings, particularly occlusive dressings of the type disclosed in U.S. Pat. No. 4,738,257 (which has a skin-contacting layer containing fluid-absorbing hydrocolloids covered by a stretchable backing layer) have been found highly effective in protecting against and treating pressure sores and dermal ulcers but, despite the flexibility of such dressings, difficulty has been encountered in conforming them to sharply curved (and shape-changing) joint areas such as the heel and elbow.

In efforts to achieve better conformity, such dressings have in the past been provided with irregular outlines. For example, a butterfly-shaped dressing known in the prior art has a central portion to be placed over the wound or ulcer and outwardly-extending wing portions that adhesively engage the surrounding skin areas. However, unless the central portion is relatively small, it cannot conform to the double curvatures of an elbow or heel surface. Should the central portion be too small, the wound may be insufficiently covered, and should it be large enough to extend over the wound, peripheral wrinkles may develop which result in channeling and leakage. Since dermal ulcers commonly exude fluids, such leakage may result in soiling, loosening of the dressing, and contamination of the wound.

It has also been known in the past to provide dressings with peripheral relief slits so that the edges of the slits may be pulled together or even overlapped as the dressing is applied, thereby shaping the dressing into non-planar configuration that more closely follows the contour of a heel or elbow. However, if such a slit is insufficiently closed, or separates in use, a direct leakage path is provided. In addition such a dressing suffers from the same disadvantage of other dressings described above, namely, that in order to prevent wrinkling or buckling of the dressing's wound-contacting central portion, that portion must be kept relatively small and, because of the radial slits and the inability of the peripheral portion to adapt to sharply curved contours, and/or changes in such contours as a joint is flexed, channeling, leakage, detachment and contamination remain serious problems.

Accordingly, an important aspect of this invention is to provide an occlusive wound dressing that is supplied to the user in planar condition but which may be easily pre-shaped to conform generally with the sharply curved contours of heel or elbow surfaces and, once in place, will remain secured with little or no risk of leakage and the problems associated with such leakage.

Briefly, the dressing comprises a layer of soft, pliant, adhesive material having particles of one or more absorbable and swellable hydrocolloids dispersed therein. A flexible and stretchable backing layer, preferably formed of a thin layer of elastomeric material, extends over one side of the adhesive layer. The opposite side of the adhesive layer is covered by a removable release sheet formed of flexible but preferably non-stretchable material such as siliconized paper or plastic film.

The dressing is contoured along the side covered by the backing layer to provide the dressing with a readily-distinguishable central portion and a relatively thin border portion surrounding the central portion. The thickness of the adhesive layer along the border portion is substantially less than the thickness of such material in the central portion, and a characteristic feature of the dressing is that it has at least one generally triangular gusset portion extending from the border portion into the central portion. The thickness of the adhesive material of the gusset portion is substantially the same as that of the border portion. After removal of the release sheet, a user may fold the gusset portion upon itself along an inwardly-extending fold line so that sections of the gusset on each side of the fold line become adhesively sealed together to form an inwardly-extending non-expandable pleat that shapes the dressing into non-planar configuration. By providing a plurality of such gussets at predetermined locations, a plurality of pleats may be formed that shape the dressing into generally anatomically-conforming configuration.

Such pre-forming of the dressing occurs prior to application of the dressing to the patient. As the pleats are formed, the dressing develops a pocket for receiving the heel or elbow of the patient, insuring that the relatively thick hydrocolloid-containing central portion of the dressing, now pre-shaped to conform generally with the heel or elbow area, will directly contact the wound and will be large enough to extend outwardly beyond the edges of the wound. Full contouring of the dressing to the wound site may then be completed after initial placement of the dressing because of the soft, compliant nature of the hydrocolloid-containing adhesive material and the flexibility and stretchability of the backing layer. Because of the thinness of the adhesive material in the border zone (the thickness of the adhesive layer in the border and gusset portions should be no greater than 0.5 mm and preferably well under 0.25 mm) and the width of the border (at least 5.0 mm), the border easily follows the contours of the skin to which it is adhered with the result that channeling and leakage are avoided or greatly reduced.

Other advantages, features and objects of the invention will become apparent from the specification and drawings.

BRIEF DESCRIPTION OF THE DRAWINGS

FIG. 1 is a plan view of a heel/elbow dressing embodying this invention.

FIG. 2 is an enlarged sectional view taken along line 2—2 of FIG. 1. The view is schematic to the extent that the thicknesses of the layers have been exaggerated for clarity of illustration.

FIG. 3 is a still further enlarged fragmentary sectional view of a gusset portion of the dressing (delineated by a phantom line in FIG. 2) depicting such gusset portion as it is folded to form a permanent, non-expandable pleat.

FIG. 4 is a perspective view of the dressing with its gussets folded to form a pair of triangular pleats, giving the dressing a non-planar and somewhat cup-shaped appearance.

FIG. 5 is a side elevational view of the pre-formed dressing depicted in FIG. 4.

FIG. 6 is a vertical sectional view showing how the dressing of FIG. 5 may be applied to a patient's heel.

DETAILED DESCRIPTION OF PREFERRED EMBODIMENT

Referring to the drawings, the numeral 10 generally designates a wound dressing particularly suitable for the care and treatment of pressure sores and dermal ulcers located on sharply-curved surfaces of a patient's body, such as at the heel or elbow. FIGS. 1 and 2 depict the dressing in a generally flat or planar condition as it would be supplied to the user. The dressing may be considered generally oval in outline with an arcuate tongue-like extension 11 and, except for the tab portions of a removable release sheet (described in detail hereinafter), the dressing is symmetrical with respect to a transverse midline 12 (FIG. 1). While the configuration shown is believed preferable, other configurations may be suitable, and it is to be understood that the particular outline is shown for illustrative purposes.

The dressing comprises at least three layers: a primary layer 13 of a hydrocolloid-containing adhesive material, a backing layer 14 of a thin, flexible and stretchable material that covers one surface 13a of the adhesive layer, and a removable release sheet 15 that covers the opposite surface 13b of the adhesive layer. The dressing is contoured with the surface 13a of the adhesive layer 13, as well as the backing layer 14 covering that surface, being shaped to define a relatively thick central portion 10a and a relatively thin border portion 10b surrounding the central portion (FIG. 1). In general outline, the central portion 10a may be oval except for one or more gusset portions 16 and 17 located along one of the longitudinal sides of the oval.

Adhesive layer 13 consists generally of one or more hydrocolloids dispersed in a viscous, water-insoluble, elastomeric adhesive binder. The hydrocolloid content may range from about 50 to 75% and may consist of any of a number of hydrocolloids such as sodium carboxymethyl cellulose, calcium carboxymethyl cellulose, pectin, gelatin, high molecular weight carbowax, carboxypolymethylene, polyvinyl alcohol, polyacrylates and other finely-divided moisture-absorbing and swellable materials dispersed in about 50 to 30% by weight of a viscous elastomer such as polyisobutylene, natural rubber, silicone rubber, acrylonitrile rubber, or polyurethane rubber. As disclosed in U.S. Pat. No. 3,339,546, an effective adhesive composition is believed to be composed of polyisobutylene in which is dispersed a mixture of approximately equal percentages by weight of sodium carboxymethyl cellulose, pectin and gelatin. A preferred adhesive composition for wound dressings that is believed to be especially suitable here is set forth in European patent application 0 621 042 published Oct. 26, 1994, the disclosure of which is incorporated herein.

Since polyisobutylene cannot be chemically or physically cross-linked, it may be desirable to include a cross-linking elastomeric resin which blends with the polyisobutylene to form a continuous elastomeric phase. Suitable resins for such purposes are the copolymer resins formed from ethylene and vinyl acetate (EVA resins). Suitable formulations of EVA with polyisobutylene are disclosed in U.S. Pat. Nos. 4,477,325 and 4,738,257.

Alternatively, the elastomeric phase may be composed or contain a cross-linking polymer such as a styrene-olefin-styrene block copolymer or an ethylenepropylene block copolymer which is capable of forming physical cross-links, so that the elastomer in solidified composition inherently provides a cross-linked network as described in U.S. Pat. No. 4,231,369.

Other ingredients may be optionally included in the adhesive formulation such as a suitable tackifier resin for improving the dry tack of the composition. Hydrocarbon tackifiers of the kind described in U.S. Pat. No. 4,231,369 may be included. In addition, oil extenders of petrolatum, paraffin oil, polybutylene oil, and vegetable oils may be included in the adhesive blend, all as well known in the art.

The backing layer 14 is both flexible and stretchable and may be in the form of a polymeric film, a non-woven or woven fabric, or a polymeric foam. Particularly effective results have been obtained with a backing layer formed of a thin film of polyurethane having a thickness of from about 0.025 to 0.1 mm, but other films having similar properties may be used. It is particularly desirable if the film or other backing material has elastomeric properties.

The use of a transparent polymeric film as the backing layer 14 is particularly advantageous because it may allow a user to see the outline of a wound through the dressing during and after application, assuming that the primary adhesive layer 13 also has sufficient transparency or translucency to provide such transmission. Where such viewing of the wound is considered unnecessary or undesirable, more opaque backing materials may be utilized. Polymeric foams of polyurethane or polyethylene may be used as well as flexible and stretchable non-woven materials of spun-bonded polyethylene and other synthetic or natural fibers.

Release sheet 15 is flexible but substantially non-stretchable and therefore not only protects the surface 13b of the adhesive layer 13 until the time of application but also helps maintain the shape of the dressing prior to use. As stated, it may be composed of siliconized paper or a suitable polymeric material such as polyethylene terephthalate (or any other polymeric film that is preferably transparent and has high dimensional stability) that has been treated or compounded to resist secure attachment to adhesive layer 13. Preferably, the release sheet 15 is provided with a line of separation 18 dividing it into two sections 15a and 15b which, in the illustration given, are of unequal size. Sections 15a and 15b include tabs 19 and 20, respectively to facilitate peeling the sections of the release sheet away from the surface of adhesive layer 13 in preparation for application.

The adhesive layer 13 is continuous, imperforate, and coextensive with backing layer 14. The thickness of the adhesive layer in the primary central portion 10a should exceed 0.5 mm, but otherwise its thickness dimension is not considered critical. The thickness of the adhesive layer along border portion 10b should be substantially less than the thickness of such material in central portion 10a and, in any event, the thickness of the adhesive material in the border portion should be no greater than 0.5 mm and preferably well under 0.25 mm. In addition, the thickness of the adhesive material of gusset portions 16 and 17 should be the same as, or similar to, the thickness of such material in the border portion. By way of example, in a particularly effective embodiment of the invention, in the form of a dressing having the appearance shown in the drawings, the adhesive layer 13 may be provided with a thickness of about 0.6 mm in its central body portion and a thickness of 0.2 mm in its border and gusset portions, with the contoured side 13 of the adhesive layer being backed by an elastomeric polyurethane film of 0.025 mm thickness.

As brought out in International patent application WO 92/05755, published Apr. 16, 1992, it is important that the border of a contoured hydrocolloid dressing have a thickness no greater than 0.5 mm and a width (in which the adhesive layer is of substantially uniform thickness) of no less than about 5 mm, preferably 10 mm or more. It has been found that such a construction prevents channels that may be formed between the skin and the relatively thick central portion of a dressing from expanding outwardly beneath the border to the extreme outer edge of a dressing. Such advantages are applicable here. In addition, the thinness of adhesive material that allows the border portion to follow the contour, and the changes in contour, of skin surfaces also allows the thin adhesive material of gussets 16 and 17 to be folded along inwardly-extending fold lines to produce permanent, non-expandable pleats that convert the planar dressing into one that conforms generally with the shape of the heel or elbow onto which it is to be placed.

As shown in FIG. 1, gusset portions 16 and 17 of the planar dressing are generally triangular in shape. The fold lines for pre-forming the dressing are represented by phantom lines 16a and 17a in FIG. 1. The folding operation is depicted in FIG. 3. After peeling away the release sheet 15, the user grips the sides of the gusset 16 (or 17) by the backing layer 14 and folds the gusset upwardly about fold line 16a (or 17a) to bring the two side sections of the gusset together. Once the adhesive side sections of the gusset contact each other, they adhere securely together to form a triangular pleat 21 that is permanent in nature because the adhesive material bonds securely to itself and prevents unfolding of the pleat. As shown in FIG. 3, the edges of the triangular gusset that delineate that gusset from the relatively thick central portion 10a of the dressing are brought together with the result that the folding action effectively obliterates the gusset, and the relatively thick central portion of the dressing continues from one side of the pleat to the other.

FIG. 4 illustrates the pre-formed dressing with its release sheet removed and both of the gussets folded upon themselves to form two triangular pleats 21. The pleats cause the dressing to assume a somewhat cup-shaped configuration defining a pocket or recess 22 for receiving the patient's heel or elbow. The triangular pleats also effectively reinforce the dressing along the same folds that are responsible for the changes in dressing configuration and, because the material of such folds is continuous and is permanently sealed together, risks of fluid leakage are avoided or substantially eliminated.

The orientation of the folded dressing in relation to a heel or elbow depends partly on the location of the ulcer or bedsore. Because of its large size, however, the central portion 10a of the dressing may effectively cover a wound whether it is located along the back of the heel (or elbow) as indicated by location x in FIG. 6, or along the bottom of the heel at location x'. In general, it is believed preferable to orient the dressing so that the tongue portion 11 is closer than the pleats 21 to the wound. Therefore, if a wound were located in position x, it is believed preferable to orient the dressing so that tongue portion 11 extends upwardly along the back of the ankle.

The dressing is pre-formed into the configuration depicted in FIGS. 4 and 5 prior to being fitted upon the patient. The configuration of the dressing as so folded approximates the configuration of the surface to be covered and, because the dressing can be further shaped by reason of the deformability of the adhesive layer 13 and the flexibility and stretchability (and preferably, elasticity) of the backing layer 14, the dressing, once applied, can be molded easily by finger pressure into firm sealing engagement with the wound and surrounding skin areas.

In the preferred embodiment shown and described above, the contouring of the adhesive layer 13 is along the side of that layer 13a covered by backing layer 14 with the opposite side 13b being non-contoured and covered by removable release sheet 15. If desired, however, the contouring may exist along both surfaces 13a and 13b. It may even be considered desirable to provide the contouring entirely on side 13b, with 13a being relatively flat or non-contoured. For purposes of this invention, it is critical that the adhesive layer 13 be contoured with one or more thin gusset portions that may be folded upon themselves to form pleats, but the side or sides along which the adhesive layer is contoured is considered less important, although preferably such contouring is provided along the side of backing layer 14 as indicated.

While in the foregoing, I have disclosed an embodiment of the invention in considerable detail for purposes of illustration, it will be understood by those skilled in the art that many of these details may be varied without departing from the spirit and scope of invention.

I claim:

1. A generally planar wound dressing for application to joint surfaces such as the heel and elbow, the dressing comprising:

an adhesive layer of soft, pliant, water absorbable and swellable material;

the adhesive layer defining:

at least one central portion;

a border portion surrounding the central portion, the border portion continuous with, and having a thickness substantially less than the central portion; and at least one generally triangular gusset portion extending from the border portion into the central portion, the gusset portion comprising an inwardly-extending fold line with sections on each side of the fold line; and a backing layer of thin, flexible material extending over and secured to one side of the adhesive layer;

whereby the gusset portion may be folded upon itself along the inwardly-extending fold line, the sections of the gusset portion being sealed together by the adhesiveness of the adhesive layer to form an inwardly-extending non-expandable pleat.

2. The dressing of claim 1 in which said backing layer is stretchable and recoverable.

3. The dressing of claim 2 in which said backing layer is formed of elastomeric film.

4. The dressing of claim 1 in which the thickness of said adhesive layer of said border portion and said gusset portion is no greater than 0.5 mm.

5. The dressing of claim 4 in which said adhesive layer of said border portion and said gusset portion has a thickness less than 0.25 mm.

6. The dressing of claim 5 in which said adhesive layer of said central portion has a thickness greater than 0.5 mm.

7. The dressing of claim 1 in which said central portion is generally oval-shaped in outline with a pair of opposite sides; said dressing being provided with two of said gusset portions along one of said sides of said oval-shaped central portion.

8. The dressing of claim 7 in which said oval-shaped central portion has a transverse midline; said triangular gusset portions being spaced apart equal distances on opposite sides of said transverse midline.

9. The dressing of claim 8 in which said border portion includes an arcuate tongue portion along an extension of said transverse midline and extending away from a side of said central portion opposite from the location of said triangular-shaped gusset portions.

10. A generally planar wound dressing for application to joint surfaces such as the heel and elbow, the dressing comprising:

a layer of soft, pliant, adhesive material having particles of one or more water absorbable and swellable hydrocolloids dispersed therein;

a backing layer of thin, flexible material extending over and secured to one side of the adhesive layer; and said adhesive layer and backing layer defining:
- at least one central portion;
- a border portion surrounding the central portion, the border portion continuous with, and having a thickness substantially less than the central portion; and
- at least one generally triangular gusset portion extending from the border portion into the central portion, the gusset portion comprising an inwardly-extending fold line with sections on each side of the fold line;

whereby the gusset portion may be folded upon itself along the inwardly-extending fold line, the sections of the gusset portion being sealed together by the adhesiveness of the adhesive layer to form an inwardly-extending non-expandable pleat.

11. The dressing of claim 10 in which said backing layer is stretchable and recoverable.

12. The dressing of claim 11 in which said backing layer is formed of elastomeric film.

13. The dressing of claim 10 in which the thickness of said adhesive layer of said border portion and said gusset portion is no greater than 0.5 mm.

14. The dressing of claim 13 in which said adhesive layer of said border portion and said gusset portion has a thickness less than 0.25 mm.

15. The dressing of claim 14 in which said adhesive layer of said central portion has a thickness greater than 0.5 mm.

16. The dressing of claim 10 in which said central portion is generally oval-shaped in outline with a pair of opposite sides; said dressing being provided with two of said gusset portions along one of said sides of said oval-shaped central portion.

17. The dressing of claim 16 in which said oval-shaped central portion has a transverse midline; said triangular gusset portions being spaced apart equal distances on opposite sides of said transverse midline.

18. The dressing of claim 17 in which said border portion includes an arcuate tongue portion along an extension of said transverse midline and extending away from a side of said central portion opposite from the location of said triangular-shaped gusset portions.

19. A generally planar wound dressing for application to joint surfaces such as the heel and elbow, the dressing comprising:
- a layer of soft, pliant, adhesive material having particles of one or more water absorbable and swellable hydrocolloids dispersed therein;
- a backing layer of thin, flexible material extending over and secured to one side of the adhesive layer;

said adhesive layer and backing layer defining:
- at least one central portion;
- a border portion surrounding the central portion, the border portion continuous with, and having a thickness substantially less than the central portion; and
- at least one generally triangular gusset portion extending from the border portion into the central portion, the gusset portion comprising an inwardly-extending fold line with sections on each side of the fold line; and
- a removable release layer covering the side of said adhesive layer opposite from said one side;

whereby the gusset portion may be folded upon itself along the inwardly-extending fold line, the sections of the gusset portion being sealed together by the adhesiveness of the adhesive layer to form an inwardly-extending non-expandable pleat.

20. The dressing of claim 19 in which said backing layer is stretchable and recoverable.

21. The dressing of claim 20 in which said backing layer is formed of elastomeric film.

22. The dressing of claim 19 in which the thickness of said adhesive layer of said border portion and said gusset portion is substantially the same and is no greater than 0.5 mm.

23. The dressing of claim 22 in which said adhesive layer of said border portion and said gusset portion has a thickness less than 0.25 mm.

24. The dressing of claim 23 in which said adhesive layer of said central portion has a thickness substantially greater than 0.5 mm.

25. The dressing of claim 19 in which said central portion is in the shape of an oval having a pair of elongated opposite sides; said dressing being provided with two of said gusset portions along one of said elongated sides of said oval-shaped central portion.

26. The dressing of claim 25 in which said oval-shaped central portion has a transverse midline; said triangular gusset portions being spaced apart equal distances on opposite sides of said transverse midline.

27. The dressing of claim 26 in which said border portion of said dressing includes an arcuate tongue portion along an extension of said transverse midline and extending away from a side of said central portion opposite from the location of said triangular-shaped gusset portions.

* * * * *